United States Patent [19]

Fukuda

[11] 4,345,601
[45] Aug. 24, 1982

[54] CONTINUOUS SUTURING DEVICE

[76] Inventor: Mamoru Fukuda, 1260 Hardy, Bridge City, Tex. 77611

[21] Appl. No.: 138,232

[22] Filed: Apr. 7, 1980

[51] Int. Cl.³ .................... A61B 17/06; A61B 17/04
[52] U.S. Cl. ............................. 128/339; 128/334 R
[58] Field of Search ................ 128/330, 339, 334 R, 128/335, 340

[56] References Cited

U.S. PATENT DOCUMENTS

| | | | |
|---|---|---|---|
| 460,138 | 9/1891 | Hornberger | 128/330 |
| 1,822,330 | 9/1931 | Ainslie | 128/334 R |
| 3,470,875 | 10/1969 | Johnson | 128/340 |
| 3,946,740 | 3/1976 | Bassett | 128/334 R |
| 4,236,470 | 12/1980 | Stenson | 128/340 |

OTHER PUBLICATIONS

Surgery, vol. 36, No. 4, 1936, "A Suture Needle with a Detachable Point", William W. L. Glenn, pp. 790–791.

*Primary Examiner*—Kyle L. Howell
*Assistant Examiner*—C. W. Shedd
*Attorney, Agent, or Firm*—Gunn, Lee & Jackson

[57] ABSTRACT

An improved suturing apparatus for continuous suturing of incised or ruptured tissues is disclosed, the preferred form including a curved or arcuate suturing needle and an appendage at the nonpointed end protruding from the needle in a direction opposite the needle tip. A slotted, arcuate sleeve with flanged ends partially encases the needle while permitting internal sliding arcuate movement, the extent of which is dictated by the length of the slot through which the needle appendage slides. A pointed needle cap having suturing thread attached thereto is placed on the tip of the suturing needle. During suturing, the needle cap with attached suturing thread is pushed through the tissues moving in an arcuate path. A grasping device in the needle sleeve retains the needle cap after the needle passes through the tissue and as the suturing needle is withdrawn from the tissue. The suturing needle extends beyond the suture into the needle sleeve end holding the needle cap and engages the needle cap, whereupon the grasping device releases the needle cap, and the suturing needle is retracted, preparing the apparatus for the next suture.

15 Claims, 16 Drawing Figures

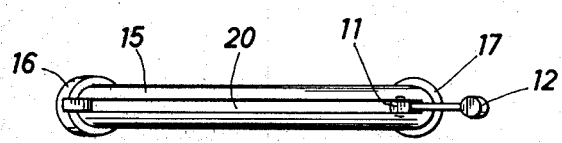
FIG. 5
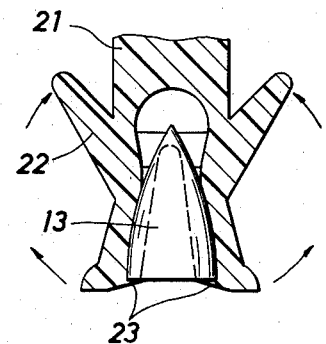
FIG. 6
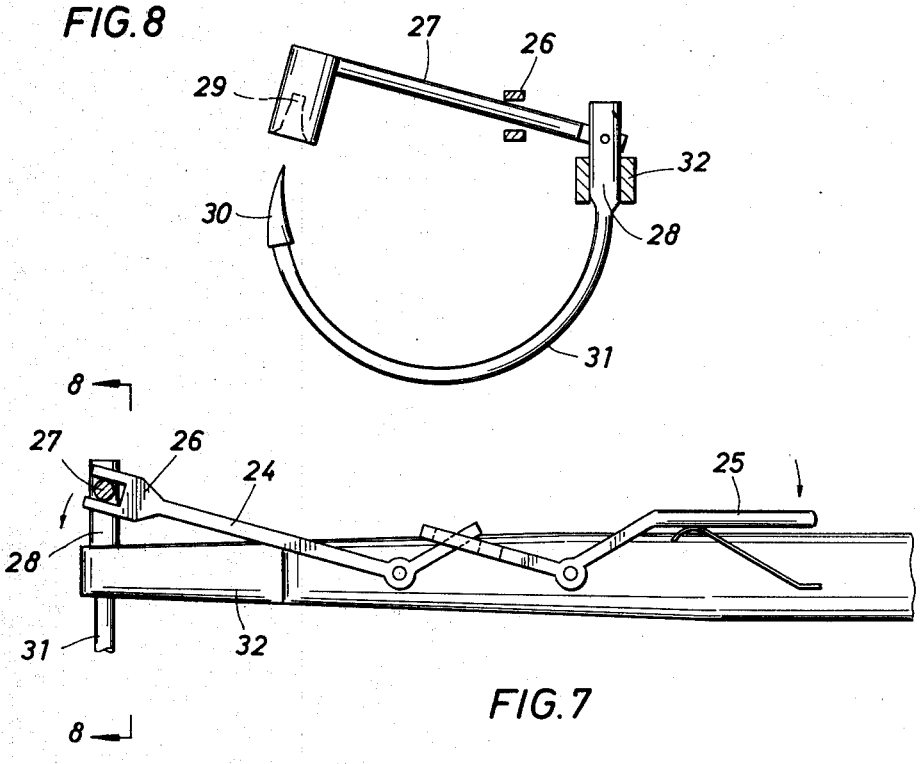
FIG. 8
FIG. 7

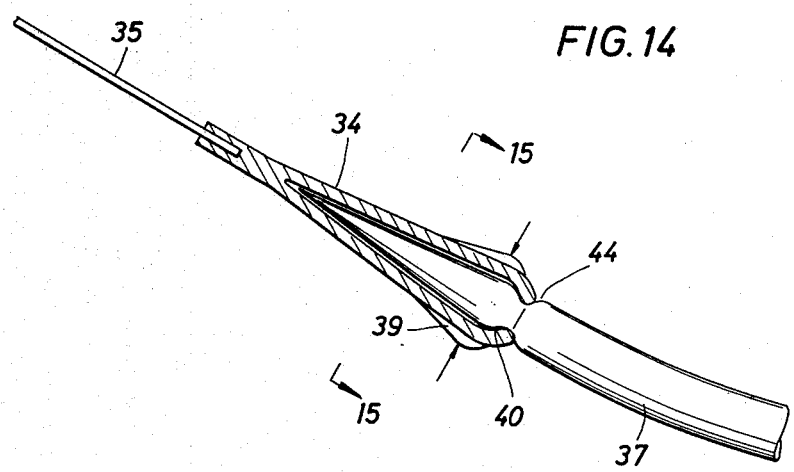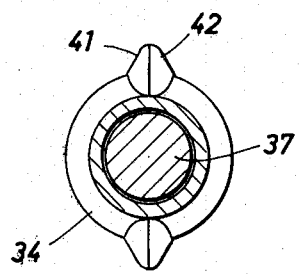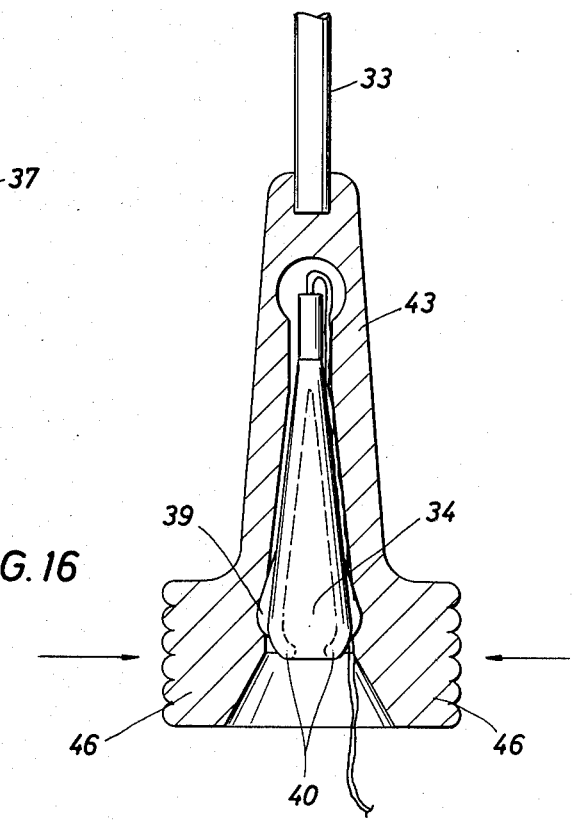

CONTINUOUS SUTURING DEVICE

BACKGROUND OF THE INVENTION

This invention pertains to an improved suturing apparatus for continuous suturing and, more particularly, to an attachable needle cap capable of carrying attached suturing thread during suturing and a suturing needle grasping device for holding such cap.

The present method of continuous suturing of ruptured or incised tissue uses a curved suturing needle with suturing thread attached to the blunt end thereof and needle-holding forceps. A typical continuous suturing operation requires numerous, even repetitive, time-consuming movements and actions. An exemplary procedure listing the steps required to complete a continuous suturing operation is as follows:

1. Suturing thread is attached to a curved suturing needle;
2. Needle-holding forceps are clamped onto the blunt end of the needle;
3. The pointed end of the needle is then inserted through the tissue to be sutured until the tip of the needle penetrates the tissue to span the incision with the needle;
4. The needle-holding forceps are unclamped from the needle;
5. The tip of the needle which has been forced through the tissue is clamped by the needle-holding forceps;
6. The needle-holding forceps are used to pull the needle through the tissue, thereby pulling the thread through the tissue; and
7. The needle-holding forceps are unclamped. Hereafter steps 2 through 7 are repeated as necessary to complete the procedure.

The continuous clamping and unclamping of the needle-holding forceps on the needle is time-consuming and an inefficient use of the user's motion. Therefore, a feature of this invention is to provide a suturing apparatus that eliminates removing and reattaching needle-holding forceps to the needle after each suture in a continuous suturing operation.

SUMMARY OF THE INVENTION

The invention includes a curved suturing needle incorporating an appendage on the blunt end which protrudes outwardly radially opposite from the tip of the needle. Needle-holding forceps may be clamped to the appendage during the suturing operation. A slotted and curved sleeve partially encloses and guides the suturing needle such that the needle appendage protrudes from and is movably restricted within the slot of the sleeve. The sleeve has flanged orifices at both ends, and, when fully extended, the needle and hollow sleeve define a complete circle with the needle partially contained at both of its ends within flanged sleeve ends. A needle cap with suturing thread attached thereto is placed over the tip of the needle, thereby drawing the suturing thread through the incised or ruptured tissue during suturing. Adequate force for the suturing needle, needle cap and suturing thread is applied through the incised or ruptured tissue by manual use of conventional needle-holding forceps clamped to the suturing needle at the handy needle appendage. Needle cap, suturing thread and needle are forced through the tissue to be sutured until the needle cap has fully exited the tissue, entered the flanged open orifice in the sleeve and has been momentarily locked therein by a grasping device. This grasping device is preferably located at the flanged orifice portion of the sleeve. A preferred grasping device is a cone-shaped holder having tension end clips with at least two inwardly flanged edges capable of expanding upon application of internally expanding force to permit entry of the needle cap and subsequent closure to capture the needle cap. Such device also includes corresponding outwardly wing-shaped tension arms which open the inwardly flanged edges to release a previously retained needle cap when external pressure is applied to the wing-shaped tension arms. The suturing needle is positioned against the retained needle cap, and pressure is applied to the wings of the tension clip to thereby release the needle cap mounted on the suturing needle tip, and the cap and needle are positioned for the next suture.

An alternate embodiment of this invention includes a curved suturing needle having a groove or indentation proximate to and circumventing the tip of the suturing needle. The needle cap includes two tension wire-type hooks or prongs extending over the orifice for encompassing the tip of the suturing needle enabling the needle cap to snap onto the suturing needle at the circumferential groove or indentation. Outwardly protruding tension wires are a corresponding part of and proximately located to the grasping end of the tension prongs such that pressure externally applied thereto causes expansion of the tension prongs and release of the suturing needle when located therein. The needle cap grasping device is preferably a flexible, cone-shaped holder having a defined area to grip and squeeze said holder releasing the suturing needle for retraction.

In one alternate embodiment, the suturing needle, alone, completely penetrates the tissue to be sutured and, upon exit, enters the needle cap grasping device enabling the needle cap to snap onto the suturing needle. The suturing needle, needle cap and suturing thread are retracted through the tissue whereupon the needle cap is transferred to the other side of the needle sleeve in preparation for the next suture. This embodiment also permits attachment of the suturing thread to the tip end of the needle cap, thereby reducing frictional resistance attributed to the suturing thread during suturing.

BRIEF DESCRIPTION OF THE DRAWINGS

So that the manner in which the above recited features, advantages and objects of the invention, as well as others which will become apparent, are attained and can be understood in detail, a more particular description of the invention briefly summarized above may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

FIG. 5 is an edge view of a preferred embodiment of the invention showing the suturing needle sliding in the needle sleeve and a slot in the needle sleeve for enabling movement of the suturing needle which view is taken along the line 5—5 of FIG. 3;

FIG. 6 is a sectional view of a preferred embodiment of the invention showing in enlarged scale the needle cap grasping device;

FIG. 7 is a side view of an alternate preferred embodiment of the invention;

FIG. 8 is a sectional view taken along the line 8—8 of FIG. 7 disclosing additional details of construction;

FIG. 14 is a view, partly in section, of an alternate embodiment of a needle cap;

FIG. 15 is an enlarged cross-sectional view taken along line 15—15 of the needle cap illustrated in FIG. 14 and including a modification; and FIG. 16 is an enlarged sectional view of an alternate preferred embodiment of the invention showing a needle cap and needle cap grasping device.

DESCRIPTION OF THE PREFERRED EMBODIMENTS

Figure 1:
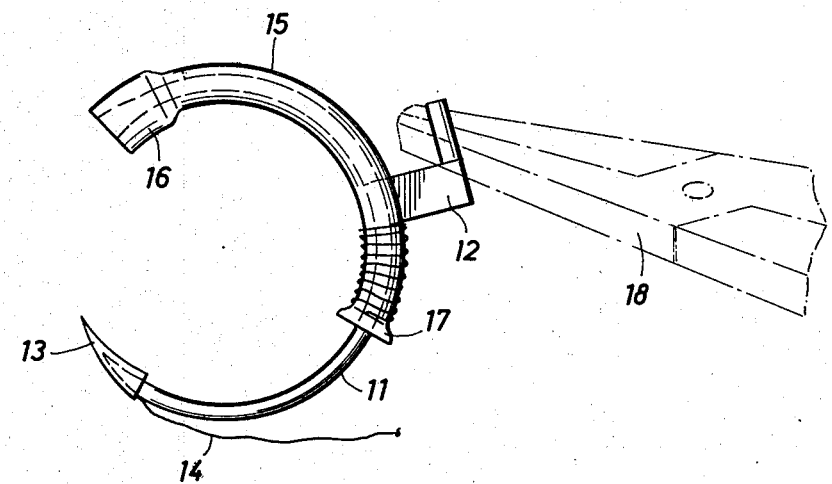
FIG. 1 is a pictorial illustration of a preferred embodiment of the invention disclosed herein.

Attention is first directed to FIG. 1 of the drawings, where an improved suturing apparatus for continuous suturing of incised or ruptured skin or tissue in accordance with the present invention is shown. An arcuately curved suturing needle 11 supports a needle appendage 12 for clamping by needle-holding forceps 18. The appendage 12 is used in the manner of a handle and, therefore, protrudes outwardly to improve its position for grasping and manipulation. A slotted needle sleeve 15 partially covers and encloses the suturing needle 11 with the needle appendage 12 protruding through and confined by a longitudinal slot in the needle sleeve 15. The sleeve has an axial passage sized to receive the needle in sliding movement. The needle has a diameter comparable to other suture needles.

A flanged end 16 is located on the end of the needle sleeve 15 proximate to the retracted blunt end of the suturing needle 11 when retracted and contains a needle cap grasping device. A similar, second flanged end 17 is located on the end of the needle sleeve 15 at the opposite end of the first flanged end 16. It is preferable that either the first flanged end 16 or the second flanged end 17 is detachable as by unscrewing to permit removal of the needle 11 for sterilization or replacement.

A needle cap 13 is placed over the tip of the needle 11 and held thereon by frictional engagement. The cap 13 is forced onto the needle point and held there by pressure of resistance of the tissue to penetration during the suturing process. It may be helpful to coat the outside of the suturing needle 11 and/or the inside of the needle cap 13 with an adhesive to prevent dislodging due to gravity when both the needle and the needle cap face downwardly. Alternately, machining the surface in the cap will rough it and improve its grip. The needle cap is sized to make as small an opening as permissible in the tissue. A coil spring shown in FIG. 1 is included to reset the needle in the needle sleeve as shown. It is omitted in several views for sake of clarity.

Figures 2, 3:
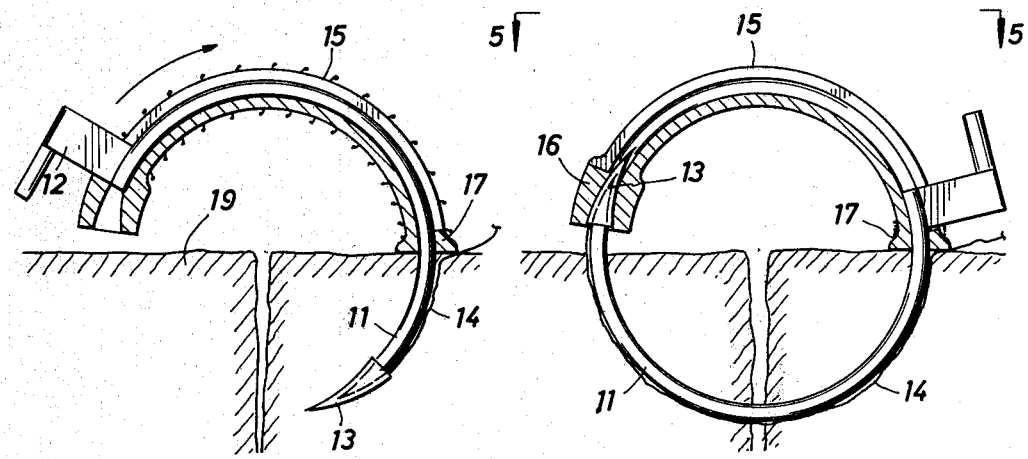
FIGS. 2–4 are pictorial illustrations of a preferred embodiment of the invention showing in series the mechanics of using the invention.
Figure 4:
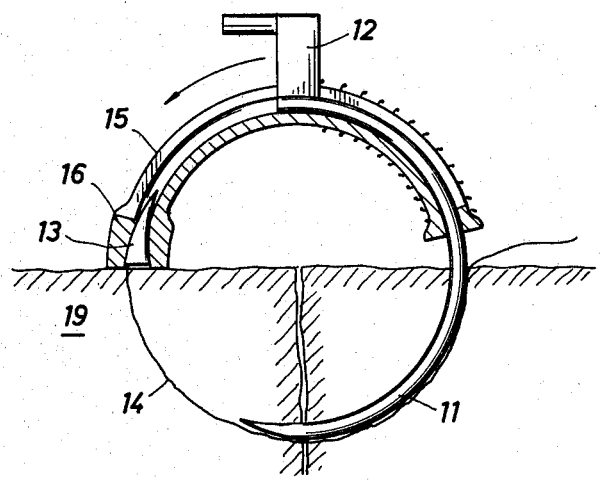

Turning to FIGS. 2-4, the mechanics of using the invention are serially illustrated. FIG. 2 illustrates the initial penetration of the needle cap 13 into the tissue 19 by the application of force on the needle appendage 12 in the direction indicated. The suturing thread 14 is carried through the tissue 19 by the needle cap 13. The flanged end 17 registers the needle sleeve 15 against the tissue 19 to protect the tiny puncture wound made by the needle.

FIG. 3 shows the suturing needle 11 in its fully extended position. The needle cap 13 has entered the flanged end 16 engaging a needle cap grasping device (described hereinafter) after completing a circular arc with the suturing needle 11. The suturing thread 14 has now been drawn completely through the incised or ruptured tissue 19.

FIG. 4 shows retraction of the needle. Movement of the needle in the direction of the arrow withdraws the suturing needle 11 from the tissue 19. The needle cap 13 with the attached suturing thread 14 is retained by a needle cap grasping device within the flanged end 16. The flanged end 16 prevents the needle sleeve 15 from puncturing the tissue 19 when the needle 11 is retracted in the illustrated manner. The needle retracts through the tissue, leaving the thread in the tissue and making a wound or small size which heals readily.

After complete retraction of the needle 11, the suturing thread 14 is pulled through the tissue 19 to the desired length, and the needle cap 13 is released and positioned on the tip of the suturing needle 11 in preparation for the next continuous suture.

FIG. 5 is a top view of the invention particularly showing the slot 20 in the needle sleeve 15. The flanged end 16 and the flanged end 17 completely encircle their respective ends of the needle sleeve 15 to capture the suturing needle 11 in the needle sleeve. The flanged ends limit the slot 20.

FIG. 6 illustrates a particularly convenient type of needle cap grasping device. As the needle cap 13 enters into a cavity within a needle cap grasping device 21, inwardly directed, diametrically opposing clips 23 are pushed aside until the blunt or nether end of the needle cap 13 has cleared the end clips which snap behind for retention of the needle cap 13. Two wing-shaped tension arms 22 are an integral part of the needle cap grasping device 21 and are attached to flex the end clips 23. When hand grip pressure is applied to the wing-shaped tension arms 22 by squeezing them toward each other, a clothespin pincher motion occurs whereby the end clips 23 open, permitting removal of the retained needle cap 13 by use of gravitational force. To this end, the device 21 is preferably formed of resilient plastic material.

FIGS. 7 and 8, together, show an alternate embodiment of the invention. A suturing needle 31 includes a needle cap grasping device 29 movably attached to the end 28 of the suturing needle 31 which has been enlarged and reinforced to provide a point of contact for the needle-holding forceps 32. This reinforcement prevents breakage of the suturing needle 31 as a result of stress.

The needle cap grasping device 29 is preferably the same device illustrated in FIG. 6. The device 29 has been illustrated in simplified form for clarity in FIG. 8. An intermediate arm 27 is pivotally connected to the enlarged end 28 of the suturing needle 31. The shown series of connected levers 24 attached to the needle-forceps 32 react to pressure exerted on a spring returned lever 25 to elevate a clevis 26 engaged with the arm 27 proximate to the enlarged end 28 of the suturing needle 31. The elevation of the needle cap grasping device 29 is dictated by the surface proximity of the tissue to be sutured. An adequate gap between the needle cap 30 and the needle cap grasping device 29 permits penetration by the needle cap 30 into the tissue without interference from the needle cap grasping device 29.

FIGS. 9-14 illustrate another alternate embodiment showing in sequence a continuous suturing operation.

Figure 9:
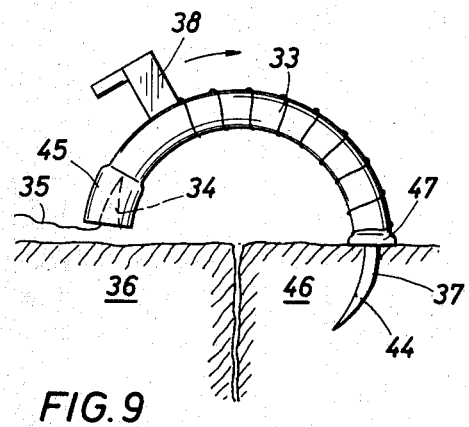
FIGS. 9-13 in sequence show use and operation of an alternate preferred embodiment of the invention.

FIG. 9 shows a modified suturing needle 37 with a needle appendage 38 at the blunt end of the suturing needle. A groove 44 slightly back from the pointed end of the suturing needle 37 is included. A slotted needle sleeve 33 partially encloses the suturing needle 37 with the needle appendage 38 protruding out of and slidable along a longitudinal slot in the sleeve. A flanged end 47 prevents the needle sleeve 33 from penetrating the tissue 46.

A second flanged end 45, opposite the pointed end of the suturing needle 37 when such needle is fully retracted into the needle sleeve 33, contains a needle cap grasping device further described hereinafter and a needle cap 34 with attached suturing thread 35.

Figure 10:
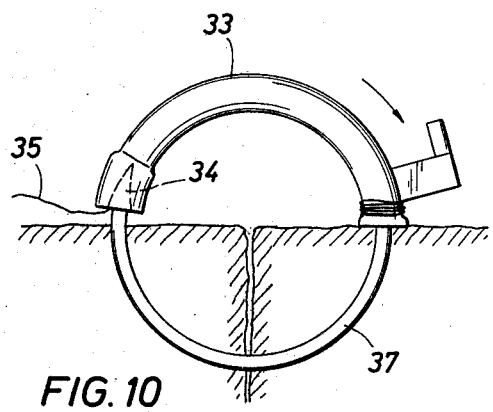

FIG. 10 shows the suturing needle 37 in a fully extended position from the needle sleeve 33 and engaging the needle cap 34 to thereby complete its circular movement. Extension and penetration of the tissue 46 by the suturing needle 37 is accomplished by directionally applied force on the needle appendage 38 by the needle-holding forceps (not shown). The needle cap 34 and attached suturing thread 35 snaps onto the suturing needle 37 as further explained hereinafter.

Figure 11:
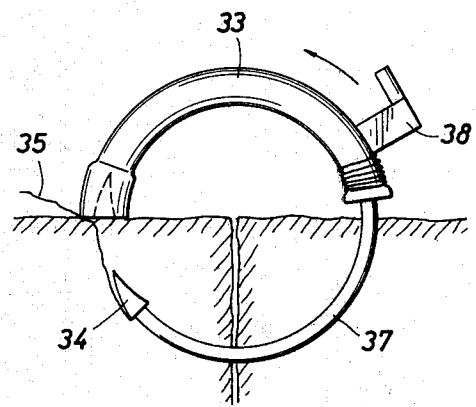

FIG. 11 illustrates partial retraction of the suturing needle 37 by directionally indicated force applied to the needle appendage 38. The needle cap 34 snapped onto the suturing needle 37 and the suturing thread 35 are also retracted therewith.

Figure 12:
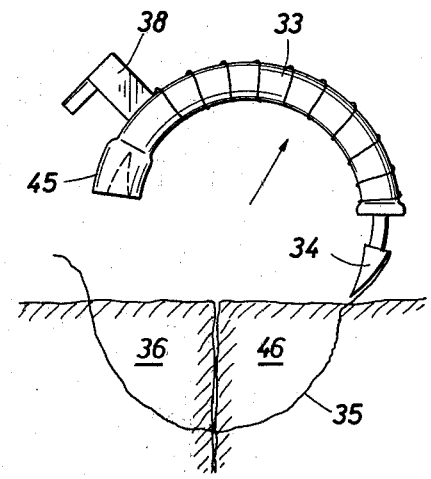

FIG. 12 shows retraction of the needle appendage 38 after the suturing needle 37 and the needle cap 34 have exited the tissue 46. Retraction draws the desired length of suturing thread 35 through the suture.

Figure 13:
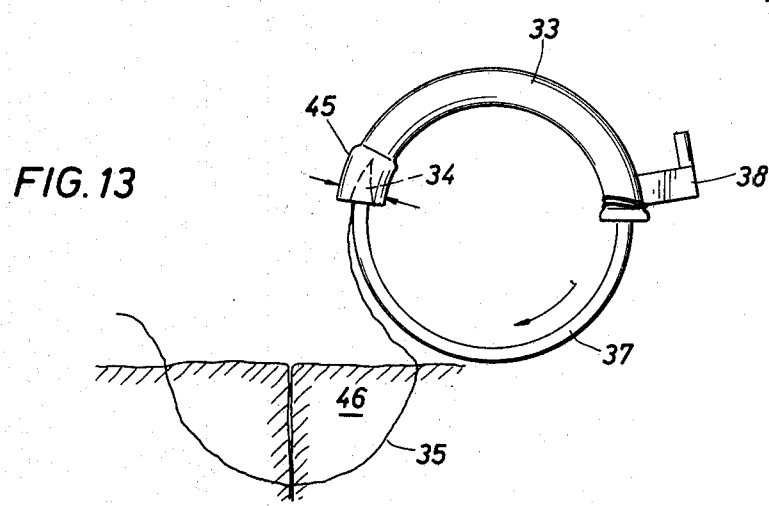

FIG. 13 illustrates return of the needle cap 34 to the flanged end 45 containing a needle cap grasping device. This step is conducted outside of the tissue 46 by movement in the illustrated direction.

Thereafter, the suturing needle 37 is released from the needle cap 34 as hereinafter described and retracted within the needle sleeve 33 to thereby prepare the apparatus for repetition of the suturing steps. Each suture is formed in the same manner. Minimal trauma occurs on needle point insertion into the tissue. On retraction of the needle point, now larger with the needle cap 34 on it, the trauma is not increased. The needle cap is preferably small, indeed, so small that trauma from penetration (see FIG. 11) is not increased.

FIG. 14 is an enlarged view of the needle cap 34 as attached to the suturing needle 37. The suturing thread 35 is preferably attached to the tip of the needle cap 34, thereby reducing the resistance as the needle is retracted through the tissue.

The needle cap 34 includes two oppositely deployed, curved hooks or prongs 40 made of spring material at the open end of the cap enabling the needle cap 34 to snap into a circumferential groove 44 found in the suturing needle 37. When the needle is fully inserted into the orifice of the needle cap 34, the hooks 40 snap into the groove 44.

Fins 39 are an integral part of and protrude outwardly from the root area where the prongs 40 attach. Hand depression of the fins 39 causes the tip ends of the prongs 40 to flex outwardly, permitting retraction of the suturing needle 37 from capture as shown in FIG. 14. The cap 34 is formed of plastic and is able to be squeezed to flex.

FIG. 15 is a cross-sectional view of the needle cap 34, illustrating a modified fin 42 having a sharp cutting edge 41 on the side of the fin 42. Suturing thread can be cut by running it over the cutting edge 41, thereby eliminating the need for a separate cutting tool which may injure surrounding tissue. Other than the modified fins, the embodiment of FIG. 15 is constructed in the same manner as that disclosed in FIG. 14.

FIG. 16 is an enlarged view of an alternate needle cap grasping device 43 contained in or as an integral part of the flanged end 45 on the needle sleeve. The needle cap grasping device 43 is preferably cone-shaped and made of a one-piece, molded, resilient material. The internal walls of the needle cap grasping device 43 are conic with an inward taper from an orifice to permit entry of the needle cap 34. The needle cap 34 is forced into the orifice of the needle cap by the suturing needle 37 (not shown). The fins 39 contact the internal walls of the needle cap grasping device 43. Hand grips 46 are manually compressed, putting pressure on the fins 39 to cause flaring of the spring loaded prongs 40 to release the needle 37 (not shown) for extraction. When the grips 46 are released, the fins 39 exert sufficient continuous outward force on the walls of the needle cap grasping device 43 to retain the needle cap 34 therein.

To minimize resistance created as the needle, needle cap and suturing thread are pushed or pulled through the tissue, the first few centimeters of the suturing thread, where attached to the needle cap, may be a fine, flexible wire.

While particular embodiments of the invention have been shown and described, it will be understood that the invention is not limited thereto since many modifications may be made and will become apparent to those skilled in the art. For example, a spring might be added internally to the needle sleeve to facilitate extension of the suturing needle, especially when the apparatus is disengaged from the tissue being sutured.

While the foregoing is directed to the preferred embodiments of the present disclosure, the scope thereof is determined by the claims which follow.

I claim:

1. A suturing apparatus for continuous suturing of incised or ruptured tissue comprising:
   (a) a curved, elongate, axially hollow sleeve having first and second ends and defining an elongate slot;
   (b) a curved suturing needle with a point, said suturing needle having a common arc and radii of curvature with said hollow sleeve and being movable relative to said sleeve between a retracted position where said needle is substantially positioned within said hollow sleeve and an extended position where said needle extends from within said first end of said sleeve into said second end of said sleeve;
   (c) a needle appendage extending from adjacent the unpointed end of said needle and through said elongate slot and defining a needle manipulating lever means located externally of said elongate sleeve;
   (d) a thread bearing cap for said point of said suturing needle adapted to connect to a suture thread; and
   (e) means for selectively separating said cap from said suturing needle point.

2. The apparatus of claim 1, wherein:
said needle manipulating lever means enables said needle to be externally engaged to be moved within said sleeve, extending said needle point in arcuate manner from aid first end of said sleeve, through tissue to be sutured and into said second end of said sleeve.

3. The apparatus of claim 2 including end located, radially flared flanges at said first and second ends of said sleeve adapted to contact against tissue during suturing.

4. The apparatus of claim 3, wherein:
said slot terminates at said flanges of said first and second ends of said elongate sleeve.

5. The apparatus of claim 1 wherein:
said means for separating said cap is supported by said sleeve and is located at said second end thereof, said means releasably engaging and holding said cap as said needle point passes through tissue in forming a suture.

6. The apparatus of claim 5, wherein:
said cap is grasped by said cap separating means by operation of a pincher movement in the wall of a receptacle for receiving said cap therein and wherein said cap is sized to fit in said receptacle.

7. The apparatus of claim 6, wherein:
said wall supports a pair of opposing grasping means to pinch about said cap.

8. The apparatus of claim 1, wherein the means for separating said needle cap from said suturing needle includes:
(a) a needle-holding forceps; and
(b) a needle cap grasping device located within said second end of said elongate sleeve.

9. The apparatus of claim 8 wherein said needle cap grasping device includes:
(a) an orifice for receipt of said needle cap;
(b) at least two inward hook means opposite each other at the mouth of said orifice; and
(c) at least two outwardly projecting wings attached to said hook means to expand said hook means to release said needle cap from said hook means.

10. A suturing apparatus for continuous suturing of incised or ruptured tissue comprising:
(a) a suturing needle including
(1) an elongate, arcuately curved needle;
(2) a pointed end and an opposite end on said needle;
(3) a protruding handle means attached to said needle near the opposite end of said needle;
(b) a needle cap fitting over the pointed end of said suturing needle; said cap being joined to a suturing thread, said cap being readily capable of puncturing said tissue when driven via said needle by said protruding handle means; and
(c) a needle sleeve including
(1) an elongate, arcuately curved encompassing sleeve;
(2) an elongate, arcuate passage in said sleeve for receiving said needle in sliding movement;
(3) a lengthwise slot in communication with said passage to enable said handle means to protrude for manipulation.

11. The suturing apparatus of claim 10 wherein said needle cap is pointed at one end.

12. The suturing apparatus of claim 10 wherein said suturing thread includes wire at the end attached to said needle cap.

13. The suturing apparatus of claim 10 including:
(a) indentation means proximate to the point of said suturing needle; and
(b) two oppositely placed hooks on said needle cap wherein said tension hooks include and are attached to corresponding fins outwardly protruding from said needle cap and are movable to expand outwardly on application of force thereto.

14. A method of continuously suturing tissue comprising the steps of:
(a) manually engaging a needle cap having suture thread connected thereto with the pointed end of a curred suture needle which is substantially positioned within a hollow curved sleeve;
(b) manually positioning said cap engaged curved suture needle adjacent to tissue at a selected point of entry;
(c) moving the needle, needle cap and suture thread along a desired path through the tissue between the point of entry and a desired exit point of the tissue;
(d) momentarily holding the needle cap and suture thread connected thereto in a needle grasping device located within the hollow curved sleeve;
(e) manually disengaging the needle from the needle cap and retracting the needle from the tissue along the same path between the exit point and the point of entry; and
(f) subsequently engaging the needle cap with the pointed end of the needle in preparation for the next suture.

15. The method of claim 14, wherein moving the needle further comprises grasping and moving a needle handle which is exposed through a slot in said curved sleeve, which sleeve guides said needle when said handle is moved.

* * * * *